(12) United States Patent
Degot et al.

(10) Patent No.: US 11,061,017 B2
(45) Date of Patent: Jul. 13, 2021

(54) HIGH THROUGHPUT AND FUNCTIONAL SCREENING METHOD FOR MUSCLE RELATED DISORDERS AND BIOLOGICAL PROCESSES

(71) Applicant: CYTOO, Grenoble (FR)

(72) Inventors: Sebastien Degot, Grenoble (FR); Yoran Margaron, Voiron (FR); Amelie Argento-Pucciarelli, Sassenage (FR); Eve Duchemin-Pelletier, Vizille (FR); Joris Michaud, La Balme de Sillingy (FR); Mathieu Fernandes, Saint-Jean de Moirans (FR); Pauline Poydenot, Saint Martine d'Heres (FR)

(73) Assignee: CYTOO, Grenoble (FR)

( * ) Notice: Subject to any disclaimer, the term of this patent is extended or adjusted under 35 U.S.C. 154(b) by 245 days.

(21) Appl. No.: 15/736,841

(22) PCT Filed: Jun. 15, 2016

(86) PCT No.: PCT/EP2016/063737
§ 371 (c)(1),
(2) Date: Dec. 15, 2017

(87) PCT Pub. No.: WO2016/202850
PCT Pub. Date: Dec. 22, 2016

(65) Prior Publication Data
US 2018/0356400 A1 Dec. 13, 2018

(30) Foreign Application Priority Data
Jun. 18, 2015 (EP) .................................. 15305946

(51) Int. Cl.
*G01N 33/50* (2006.01)
(52) U.S. Cl.
CPC ..... *G01N 33/5088* (2013.01); *G01N 33/5061* (2013.01); *G01N 33/5082* (2013.01); *G01N 2500/10* (2013.01)
(58) Field of Classification Search
None
See application file for complete search history.

(56) References Cited

U.S. PATENT DOCUMENTS

2008/0299086 A1  12/2008  Kanzaki et al.
2016/0312187 A1* 10/2016  Fernandes .............. C12M 21/08

FOREIGN PATENT DOCUMENTS

| JP | 2010-184879 | 8/2010 |
| JP | 2015-38100 | 2/2015 |
| WO | WO 2010/010127 | 1/2010 |
| WO | WO 2011/007866 | 1/2011 |
| WO | WO 2015/091593 | 6/2015 |

OTHER PUBLICATIONS

Rimann et al., CHIMIA, 69(1/2):65-67 (2015) (Year: 2015).*
Serena et al., Integrative Biol., 2(4): 193-201 (2010) (Year: 2010).*
Balghi et al., J. Gen. Physiol. 127:171-182 (2006) (Year: 2006).*
Cabrera et al., JBC, 287(27):22759-22770 (2012) (Year: 2012).*
Engler et al., JBC, 166(6):877-887 (2004) (Year: 2004).*
Guo et al., Biomater. Sci., 2(1):131-138 (2014) (Year: 2014).*
Imbert et al., Cell Calcium, 18:177-186 (1995) (Year: 1995).*
Jacot et al., Biophys. J., 95:3479-3487 (2008) (Year: 2008).*
Kim et al., Dev. Dyn., 237(10): 2830-2843 (2008) (Year: 2008).*
Marchand et al., Exp. Cell Res., 297:363-379 (2004) (Year: 2004).*
Molnar et al., Biotechnol. Prog., 23(1): 265-268 (2007) (Year: 2007).*
Nagamine et al., Biotechnol. Bioeng., 105:1161-1167 (2010) (Year: 2010).*
Nagamine et al., Lab Chip, 11:513-517 (2011) (Year: 2011).*
Porter et al., JBC, 277(32):28942-28947 (2002) (Year: 2002).*
Rufini et al., Biochem. Biophysc. Res. Comm., 238:361-366 (1977) (Year: 1997).*
Ruegg et al., Neuromus. Dis., 12:S155-S161 (2002) (Year: 2002).*
Shimizu et al., Biomed. Microdevices, 12:247-252 (2010) (Year: 2010).*
Shimizu et al., J. Biosci. Bioeng., 109(2): 174-178 (2010) (Year: 2010).*
Stiber et al., Cell Calcium, 49:341-349 (2011) (Year: 2011).*
Wang et al., Cell Calcium, 45:29-37 (2009) (Year: 2009).*
Zatti Thesis (2012) (Year: 2012).*
Cui et al., Biotechnol. Lett., 35:315-321 (2013) (Year: 2013).*
Basset et al., Biochem. J., 395:267-276 (2006) (Year: 2006).*

(Continued)

*Primary Examiner* — Thomas J. Visone
(74) *Attorney, Agent, or Firm* — Saliwanchik, Lloyd & Eisenschenk

(57) ABSTRACT

The invention relates to a method for high throughput screening compounds by using a plurality of automated cell based assays assessing skeletal muscle cells contractility, morphology, and metabolism, in order to predict the efficacy of said compound on a panel of applications linked with muscle physiological and pathophysiological processes, comprising: (i) providing an in vitro culture of myotubes, wherein the in vitro myotubes culture is obtained by the following method: providing a cell culture device allowing the culture of myoblasts or myotubes, depositing said cells from a human donor or human group of donors, in good health or affected by a muscle related disorder, from primary cells, a cell line, an isogenic cell line or differentiated stem cells recapitulating a muscle disorder, on said culture device by using a method allowing the spatial control of cell culture, culturing said cells during a determined incubation time so as to promote a spatially controlled myotube culture; (ii) adding at least one compound to said culture; (iii) after a determined incubation time of the myotubes with said compound, carrying out structural and/or functional readouts of the myotubes to determine the effect of said compound on the myotubes; and (iv) based on said determined effect, predicting the ability of said compound to improve or alter healthy muscle features, or to treat, rescue, or cure muscle disorders, said features or said disorders being linked with muscle contraction, muscle morphology or muscle metabolism.

16 Claims, 10 Drawing Sheets

(56) References Cited

OTHER PUBLICATIONS

Cintra-Francischinelli et al., Cell. Mol. Life Sci., 66:1718-1728 (2009) (Year: 2009).*
Gross et al., Skel. Mus., 3(10): 1-11 (2013) (Year: 2013).*
Ducreux et al. JBC, 279(42): 43838-43846 (2004) (Year: 2004).*
Sweeny et al., PNAS, 95:14406-14410 (1998) (Year: 1998).*
Vandenburgh et al., (FASEB J., 23:3325-3334 (2009) (Year: 2009).*
Alamdari, N. et al. "Resveratrol prevents dexamethasone-induced expression of the muscle atrophy-related ubiquitin ligases atrogin-1 and MuRF1 in cultured myotubes through a SIRT1-dependent mechanism" *Biochemical and Biophysical Research Communications*, 2012, pp. 528-533, vol. 417, No. 1.
Christensen, R. A. et al. "Calcium Dyshomeostasis in β-Amyloid and Tau-bearing Skeletal Myotubes" *The Journal of Biological Chemistry*, Dec. 17, 2004, pp. 53524-53532, vol. 279, No. 51.
Rakhilin, S. et al. "Electrical Impedance as a Novel Biomarker of Myotube Atrophy and Hypertrophy" *Journal of Biomolecular Screening*, Apr. 14, 2011, pp. 565-574, vol. 16, No. 6.
Sampaolesi, M. et al. "Stretch-induced cell damage in sarcoglycan-deficient myotubes" Pflügers Archiv—*European Journal of Physiology*, May 18, 2001, pp. 161-170, vol. 442, No. 2.
Written Opinion in International Application No. PCT/EP2016/063737, dated Sep. 12, 2016, pp. 1-8.

* cited by examiner

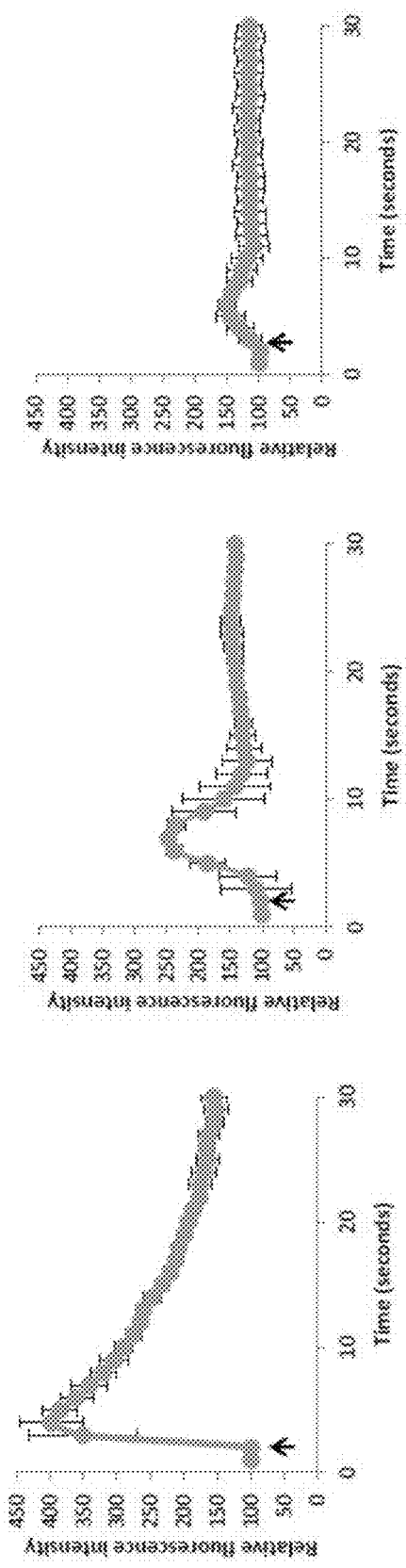
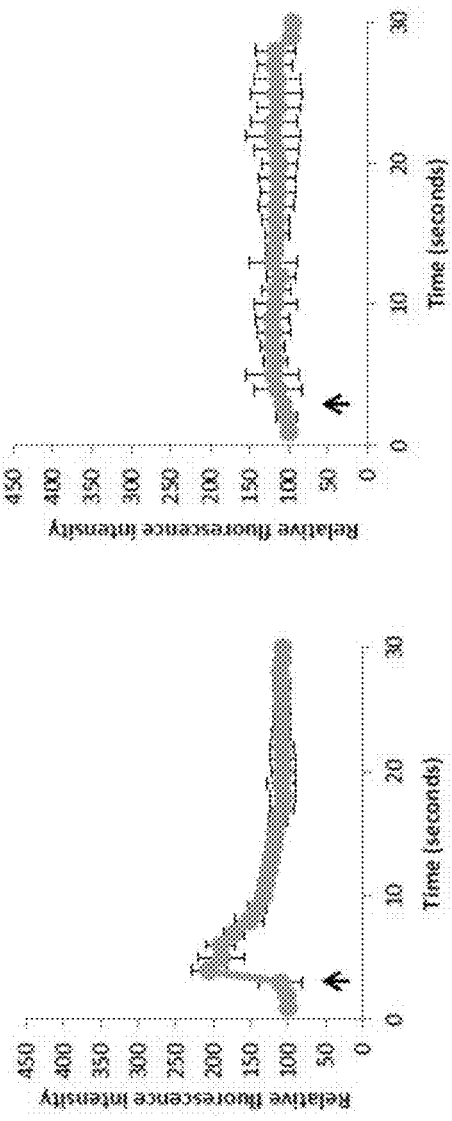
FIG. 3A Acetylcholine induction  FIG. 3B 4-Chloro-m-Cresol induction  FIG. 3C Caffein induction
FIG. 3D KCl induction  FIG. 3E IGF-1 induction

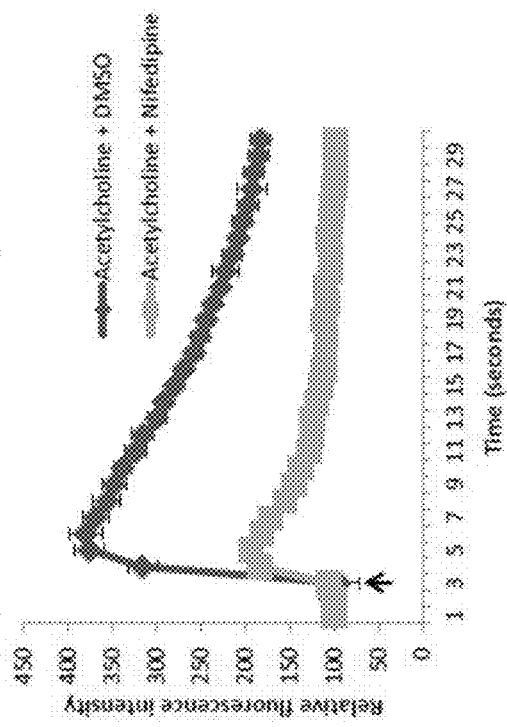
FIG. 4B Acetylcholine induction + Nifedipine
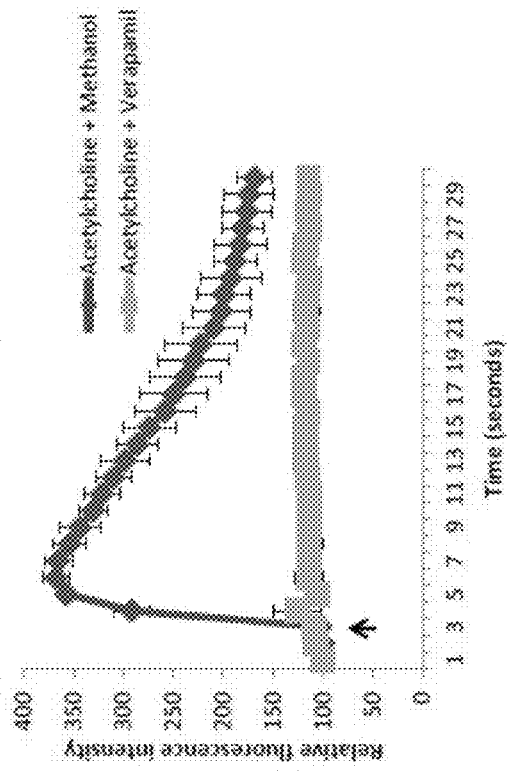
FIG. 4A Acetylcholine induction + Verapamil
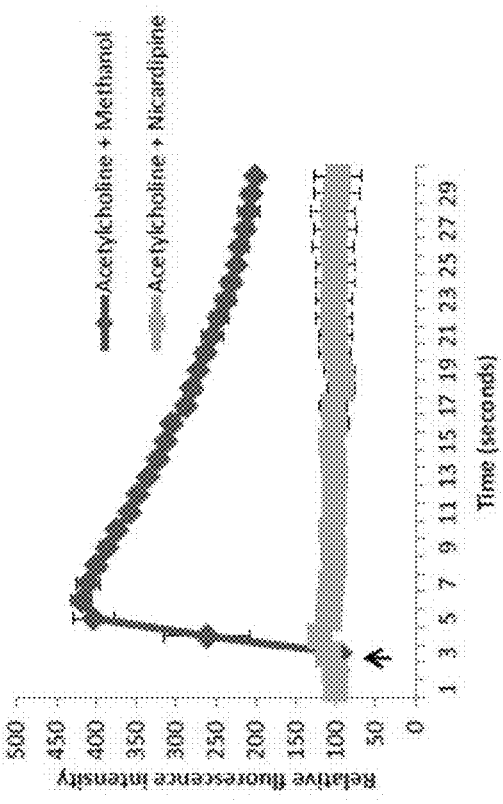
FIG. 4C Acetylcholine induction + Nicardipine

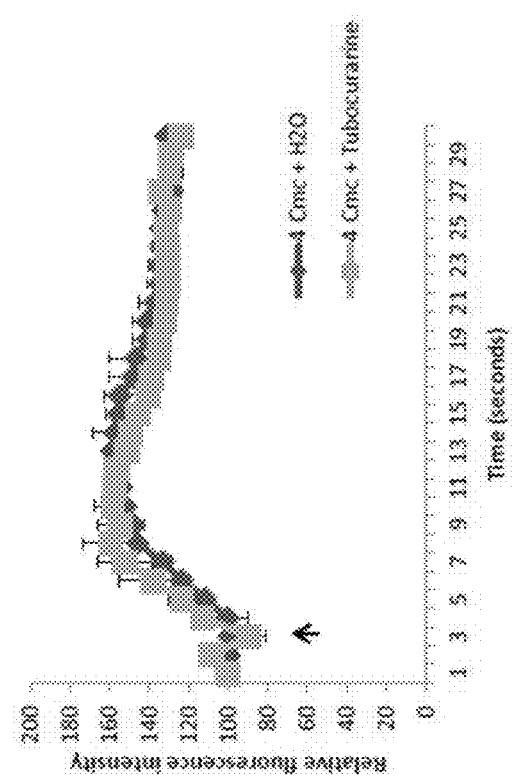
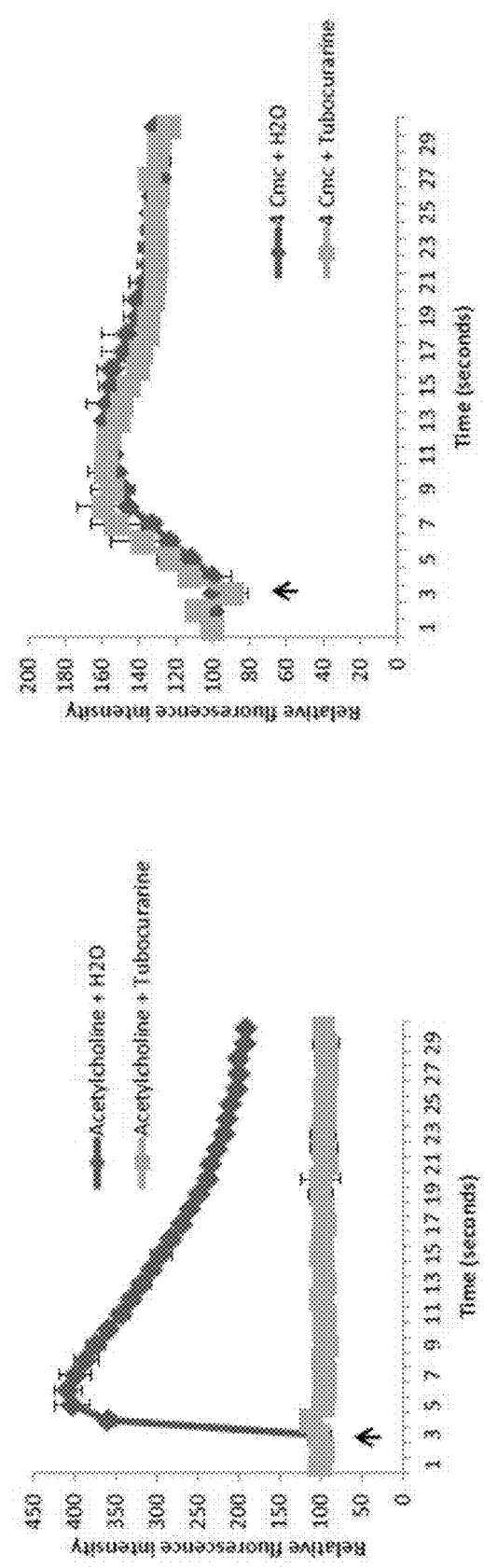
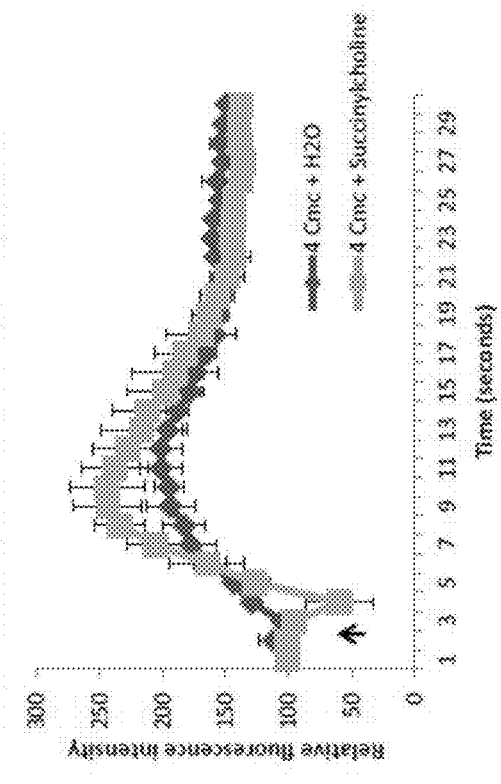
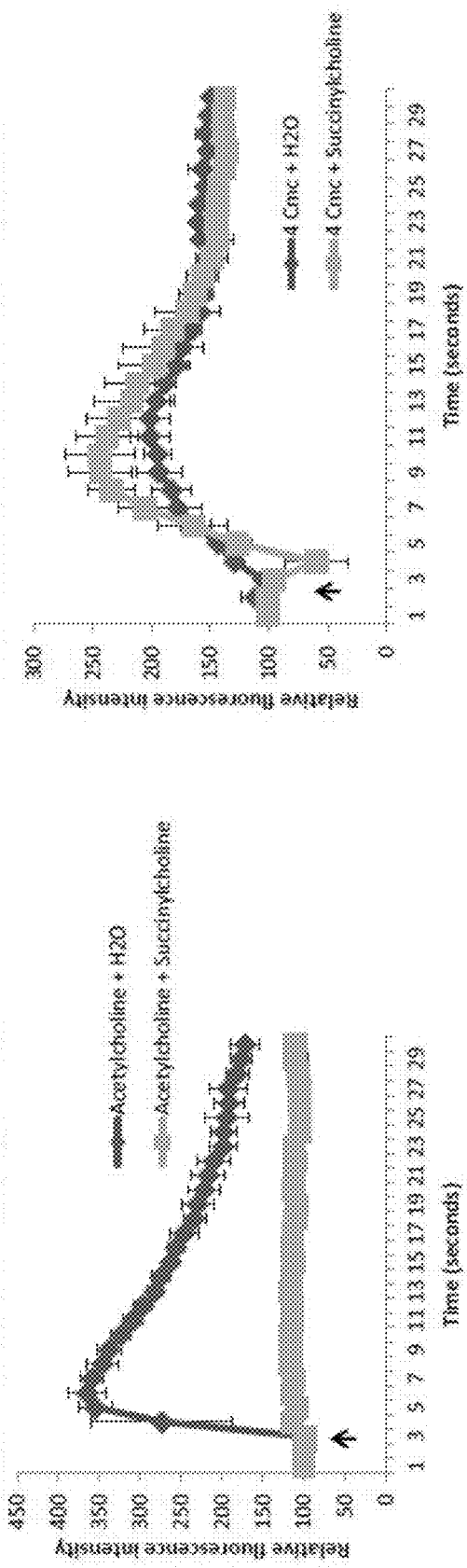

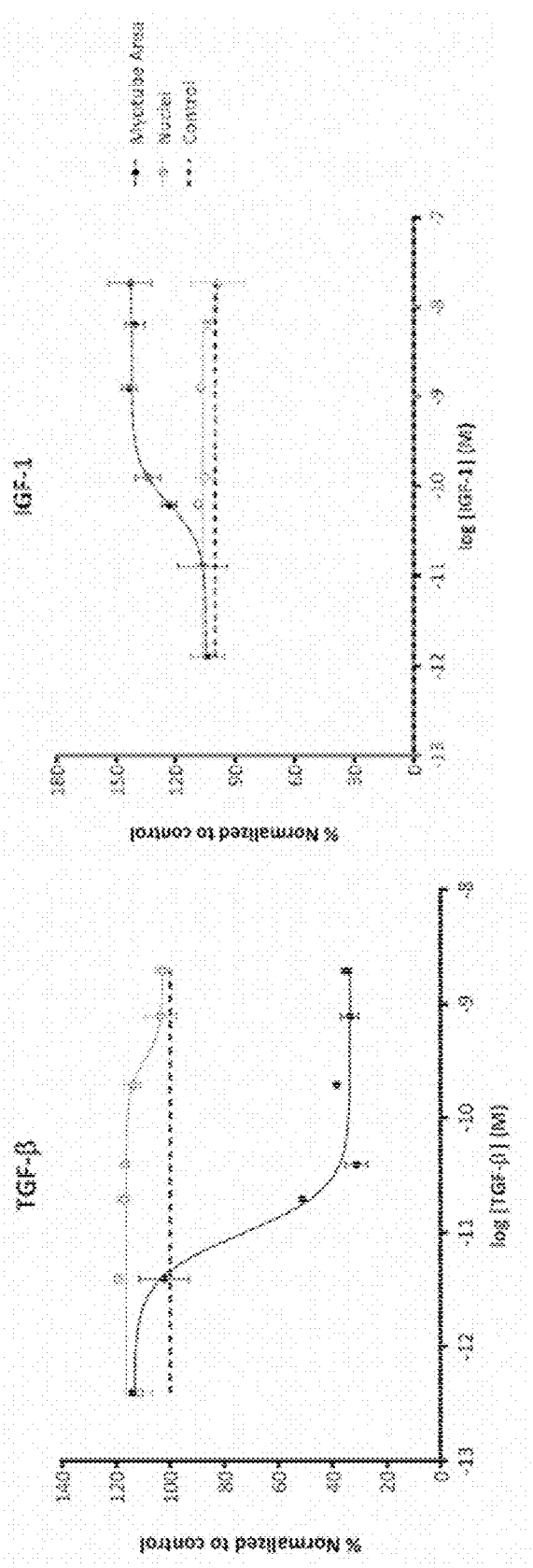
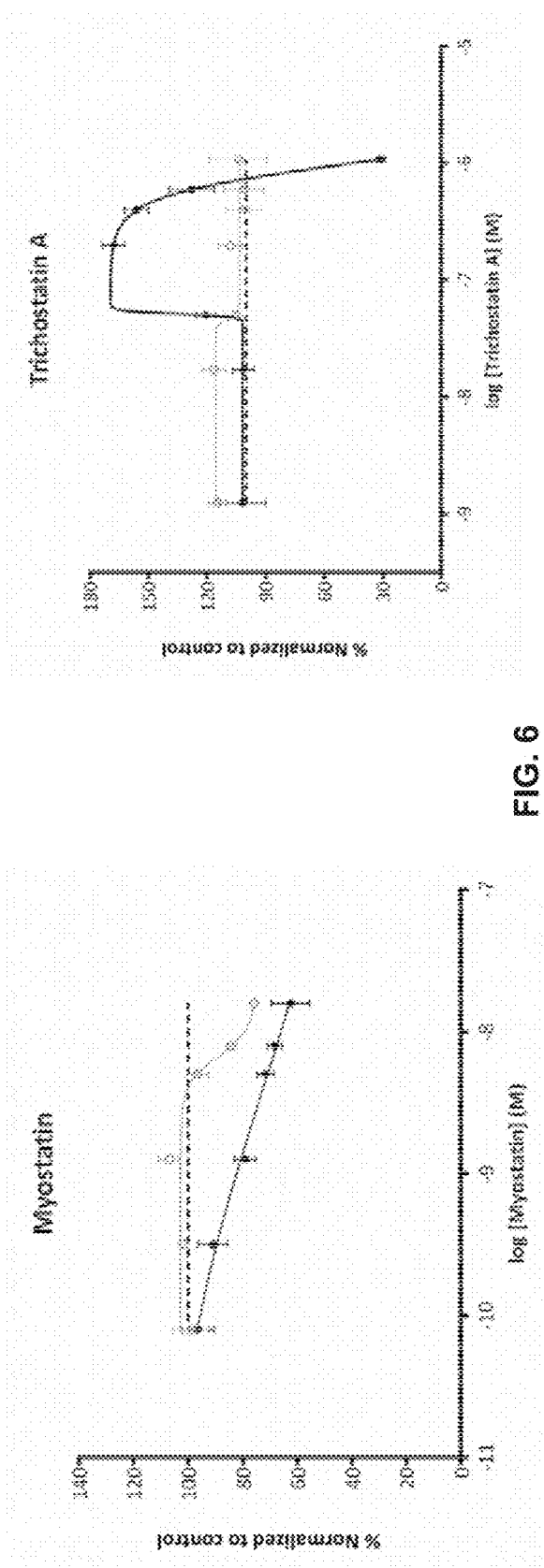
FIG. 6

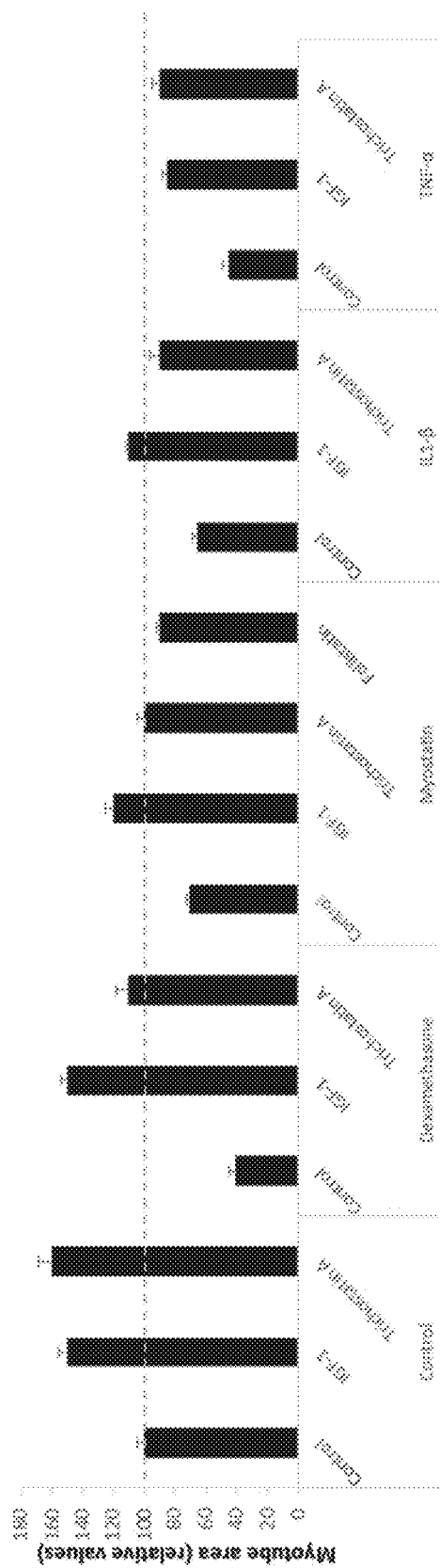
FIG. 7A
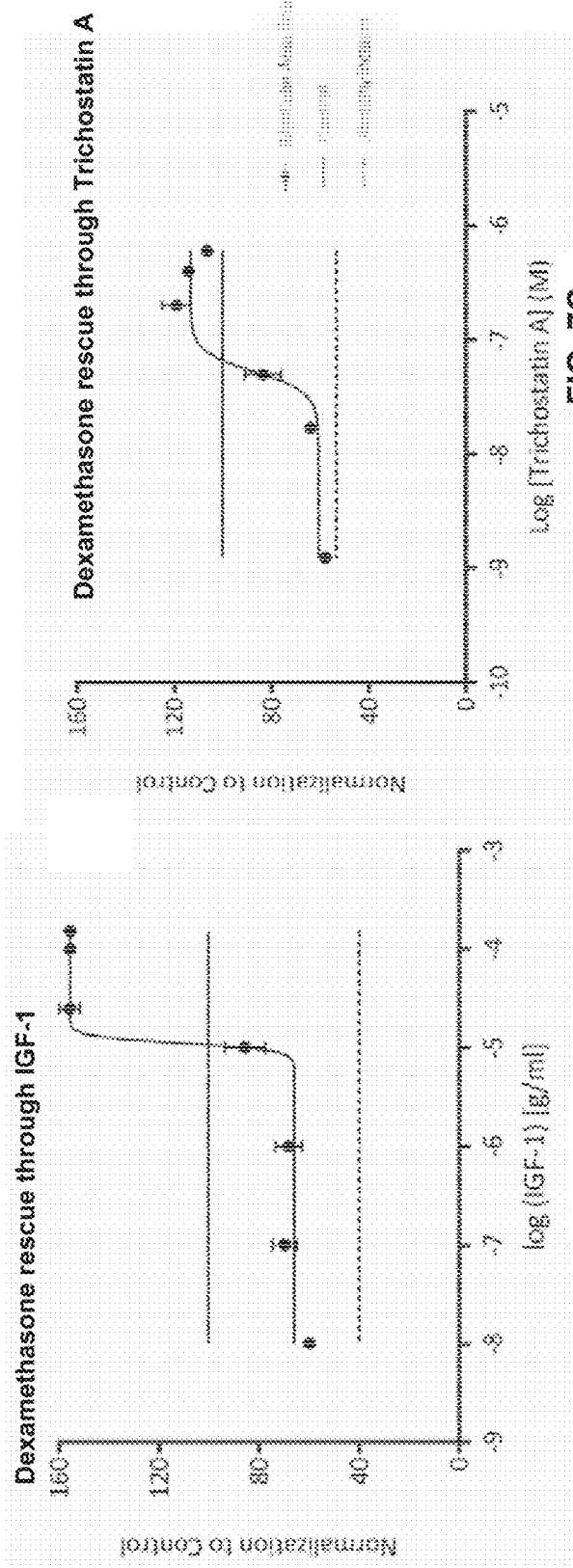
FIG. 7C
FIG. 7B

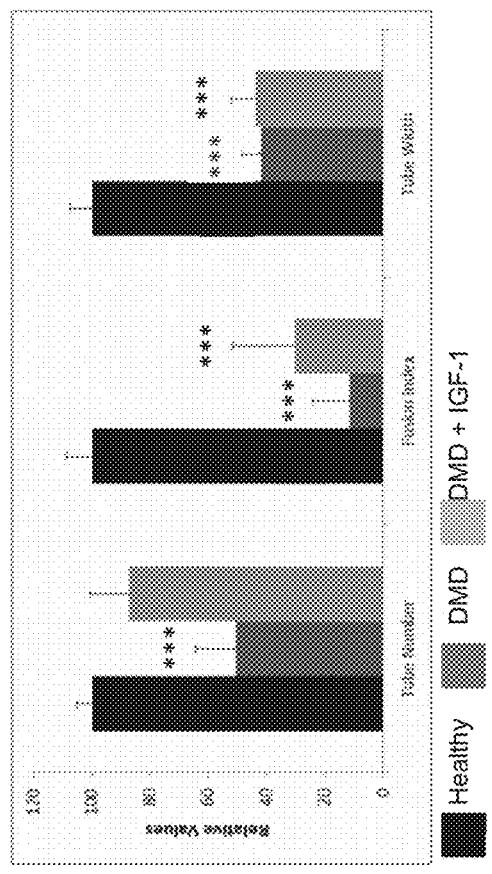
FIG. 8A Morphological rescue of DMD myotubes through IGF-1 treatment
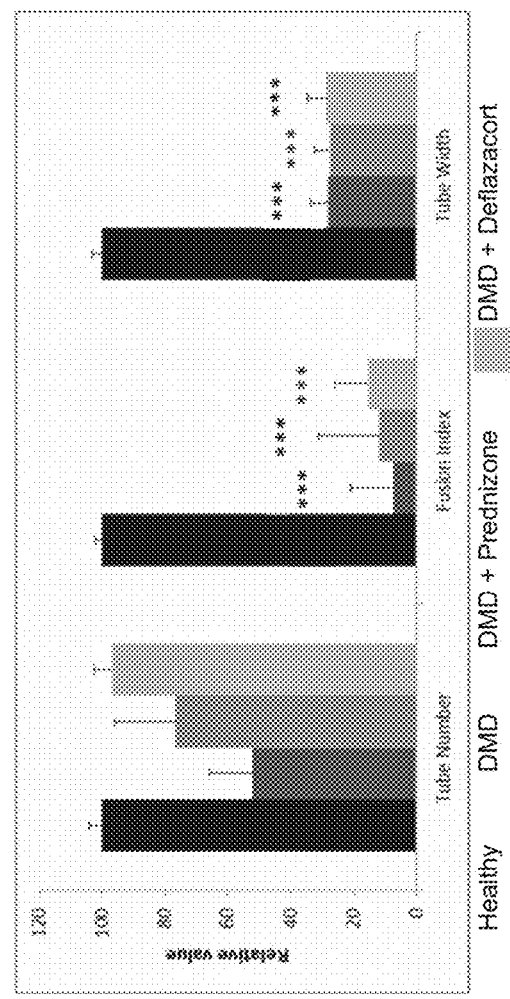
FIG. 8B Morphological rescue of DMD myotubes through Prednizone, Deflazacort and Ataluren treatments

HIGH THROUGHPUT AND FUNCTIONAL SCREENING METHOD FOR MUSCLE RELATED DISORDERS AND BIOLOGICAL PROCESSES

CROSS-REFERENCE TO RELATED APPLICATION

This application is the U.S. national stage application of International Patent Application No. PCT/EP2016/063737, filed Jun. 15, 2016.

FIELD OF THE INVENTION

The invention relates to a method allowing automated in vitro culture of single contractile muscle subunit counterpart, termed "myotube", presenting a functional motor maturity; a method to recapitulate muscle weakness in vitro; and a method dedicated to high throughput drug discovery by screening compounds in order to predict a potential effect on muscle weakness selected biological and physiopathological fields by allowing a targeted phenotype through structural and functional readouts assessing human myotube morphology, structure, contraction and metabolism.

BACKGROUND OF THE INVENTION

Muscle "weakness" is defined as a lack of strength, and has to be discerned from "fatigue". Muscle weakness is a primary symptom of muscle "wasting" and "disuse", two terms respectively meaning muscle "loss" and "not used".

In pathological situation, a reduction of the skeletal muscle mass can directly result from neuromuscular disorders such as genetic myopathies and neuromuscular junction (NMJ) diseases.

Muscular dystrophies represent a large group of myopathies causing a progressive degeneration of myofibers, the contractile muscle subunits, and resulting in a loss of muscle mass. Mutations in over 30 genes causing muscular dystrophies have been identified. These pathologies are clinically classified into the following groups: dystrophinopathies (Duchenne and Becker muscular dystrophies), Limb-Girdle dystrophies, congenital muscular dystrophies, facioscapulohumeral dystrophies, myotonic dystrophies, oculopharyngeal muscular dystrophies, distal myopathies, and Emery-Dreifuss muscular dystrophy [1]. Duchenne Muscular Dystrophy (DMD) is a recessive X-linked dystrophinopathy due to a lack of native dystroglycan complex, composed of dystrophin, alpha-syntrophin and dystroglycan [2]. Misregulation of NF-κB signalling pathways [3], as well as lactate deshydrogenase activity [4] has been characterized.

NMJ disorders correspond to a vast group of diseases affecting the control of muscle voluntary movement. These diseases essentially encompass three classes of heterogeneous disorders: genetic mutations (amyotrophic lateral sclerosis, spinal muscular atrophy and congenital myasthenic syndromes), autoimmune diseases (myasthenia gravis, Lamber-Eaton syndrome, Guillain Barré syndrome), and toxic processes (botulism, poisoning), which have in common the perturbation of the neurotransmission at the NMJ. Symptoms are characterized by progressive weakness due to a reduced muscle strength [5].

Anorexia nervosa, a psychiatric disorders leading to food starvation, is also associated with muscle atrophy [6].

Moreover, muscle loss can indirectly occur from disuse in patients because of a reduction of their ambulation or a confinement to bed during hospitalization. Resulting atrophy, named as "cachexia", is a co-morbidity factor of common diseases. Incidence in cachexia syndrome is very high in cancers from different origins (gastric, pancreatic, lung, prostate, colon, breast, leukemia) [7], but can also take origin from AIDS, obstructive pulmonary disease, kidney failure, heart failure, rheumatoid arthritis, sepsis [3, 8]. Metabolic adaptation in starved and diabetic muscles is recognized as a hallmark of an energy-wasting syndrome that leads to muscle loss and atrophy occurring in acute condition [3]. Side effects through treatments can also provoke muscle weakness. For example, statins are molecules considered to be the most efficient drugs for the treatment of hypercholesterolemia, the main risk factor for atherosclerosis. The most severe adverse effect of statin therapy is a myotoxicity resulting in myopathy, myalgia, myositis and rhabdomyolysis [9].

Finally, in human healthy population, muscle loss occurs physiologically with aging and is a component of the frailty syndrome. Named "sarcopenia", this degenerative loss results in direct muscle atrophy and subsequently weakness [10]. Structural and functional alterations in synapses due to sarcopenia also affect NMJs by inducing acetylcholine receptors (AChR) fragmentation at the postsynaptic membrane [11], consequently impairing muscle integrity and causing loss of motor tissue. Age related decline in motor performance is also at the origin of dysregulations in muscle strength causing wrinkles [12].

Many animal models recapitulating these disorders have been created in different species. However, in most cases, these models poorly phenocopy the human diseases because of genetic and physiological differences of the neuromuscular systems. For example, the human genome contains 2 SMN genes (SMN1 and SMN2) whereas all species used to model spinal muscular atrophy have one SMN gene that is equivalent to SMN1. In all organisms except Human, loss of SMN results in embryonic lethality which has led to the development of complex genetic models. In addition, transgenic mice have been engineered so that the causative gene if known is deleted rather than reproducing human mutations which also adds possible confusions in the analysis of the pathology. The existence of compensatory mechanisms in the animal models limits their relevance for human pathology. Moreover, the use of animal model is poorly compatible with large campaigns in drug discovery, and not in line with the current restrictions for compound testing on animal model. All this could explain that whereas in the last decade, progress has been made towards the development of therapeutics, there is still no curative treatment for most neuromuscular diseases [13].

In this context, an alternative is to generate in vitro models recapitulating targeted human pathologies. Muscle explants extracted from murine and human origins were extensively used in vitro to study neuromuscular diseases [14]. However, the use of tissues extracted from animals presents the same limited relevance to human as presented above, essentially because of discrepancies of physiopathologies between different species. Moreover, because of the rarity of human pathological tissues, and poor ethical insights, these models are not compatible with large scale cell based assays and screening approach for drug discovery.

Human primary myoblasts isolated from patient biopsies provide the most pertinent experimental models to assess a variety of human genetic mutations in their natural genomic environment. Although in vitro models do not fully recapitulate the in vivo environment, such cell-culture systems allow rapid, high-throughput screening of molecules. In addition, new strategies can be easily tested prior to validation in animal models, which is a costly and time-consuming process. The main drawback of using in vitro primary cultures of human cells derived from muscle biopsies are ethical insights to extract tissue from fragile patients, the rarity of some pathologic tissues, the purity of extracted cells, their limited proliferative capacity, and the variation in phenotype when amplified in vitro as their phenotype can be confounded by modifications due to cellular senescence, which will progressively occur during cell amplification [15]. To date, a very large panel of cell models mimic previously described disorders and pathologies, but many of them only focused on precursors myoblasts and fail to recapitulate the contractile muscle subunit, the "myofiber", or its in vitro counterpart named "myotube". In addition, Group of D. J. Glass recently developed a model mimicking sarcopenia using differentiated myotubes from healthy human skeletal myoblasts [16]. This group, as others, was able to measure the diameter of cultured myotubes by conventional image processing techniques [17] but resulting models are not dedicated to cell based assays or high content screening because of a lack of automation and robustness. Moreover, these measurements cannot be multiplexed with functional readouts on contractility. Another group developed a high content screening platform dedicated to traction forces measurements of groups of human myotubes differentiated in tridimensional hydrogels [18, 19]. However, this device is not compatible with measurements on individual myotubes, regarding the impossibility to individualize the myotubes embedded within hydrogels. In addition, by using this device, the response to a drug treatment is global from a myotube bundle, which does not correspond to in vivo "muscle fascicle" unit because of large structural and functional discrepancies between the two structures [20]. Consequently this model fails to describe compound effects both on muscle fascicule as well as myofiber subunits.

SUMMARY OF THE INVENTION

The invention provides a method for high throughput screening compounds by using a plurality of automated cell based assays assessing skeletal muscle cells contractility, morphology, and metabolism, in order to predict the efficacy of said compound on a panel of applications linked with muscle physiological and pathophysiological processes, comprising:
(i) providing an in vitro culture of myotubes, wherein the in vitro myotubes culture is obtained by the following method:
  providing a cell culture device allowing the culture of myoblasts or myotubes,
  depositing said cells from a human donor or human group of donors, in good health or affected by a muscle related disorder, from primary cells, a cell line, an isogenic cell line or differentiated stem cells recapitulating a muscle disorder, on said culture device by using a method allowing the spatial control of cell culture,
  culturing said cells during a determined incubation time so as to promote a spatially controlled myotube culture,
(ii) adding at least one compound to said culture,
(iii) after a determined incubation time of the myotubes with said compound, carrying out structural and/or functional readouts of the myotubes to determine the effect of said compound on the myotubes,
(iv) based on said determined effect, predicting the ability of said compound to improve or alter healthy muscle features, or to treat, rescue, or cure muscle disorders, said features or said disorders being linked with muscle contraction, muscle morphology or muscle metabolism.

According to an embodiment, said method comprises, in the myotube culture step, adding at least one muscle atrophic inducer, or performing a genetic modification, to said culture to mimic muscle wasting, disuse, or muscular genetic disease.

According to an embodiment, said method comprises, in the myotube culture step, adding at least one inhibitor of muscle contraction, or performing a genetic modification, to said culture to mimic neuromuscular disease, poisoning or muscular genetic disease.

According to an embodiment, the method comprises, in myotube culture step, adding at least one inhibitor of muscle metabolism, or performing a genetic modification, to said culture to mimic metabolism disease, or muscular genetic disease.

The method allowing the spatial control of cell culture may include bioprinting.

According to an embodiment, the cell culture device comprises a substrate and at least one cell-adhesive pattern, myoblasts from a human donor or group of human donors, in good health or affected by a emblematic muscle disorder, from a cell line, an isogenic cell line or differentiated stem cells recapitulating a muscle disorder are deposited on the at least one cell-adhesive pattern, and said myoblasts are cultured in a differentiation medium during a determined incubation time so as to promote cell differentiation into myotubes.

The substrate may be selected from:
a hard substrate and
a soft substrate wherein the Young's modulus of the substrate is comprised between 5 and 15 kPa.

According to an embodiment, the method comprises carrying out image analysis of the myotubes to measure morphological changes in skeletal muscle cells and in particular myotubes or myoblasts, said measured morphological changes comprise the area and the maximal width of the myotubes after incubation with the compound and wherein image analysis comprises myotube image binarization, computation of a distance map of said myotubes and computation of the maximal width of each myotube from said distance map.

According to an embodiment, the functional readouts comprise biomarkers of myotube maturation, through the expression and localisation of myosin heavy chain, troponin T, dystrophin, alpha-syntrophin, dystroglycans, acethycholin receptors, Smad 2/3, and/or NF-κ3.

According to an embodiment, the functional readouts comprise calcium release, and resulting myotube shortening in a high throughput assay through the quantification of the number of spots corresponding to the detachment and folding of at least one extremity of the myotubes.

According to an embodiment, the functional readouts comprise myotube metabolism through the quantification of glucose uptake, mitochondrial potential, and/or lactate deshydrogenase in a high throughput assay.

In the field of drug discovery, the method can be implemented for:
  identifying therapeutic compounds acting on atrophy or hypertrophy of skeletal muscle cells, wherein the image analysis is carried out to determine the effect of said compounds in terms of atrophic or hypertrophic properties;
  identifying therapeutic compounds acting on the maturation of skeletal muscle cells, wherein an automated analysis is carried out to determine the effect of said compounds in terms of said specific biomarkers expression and/or localisation;

identifying therapeutic compounds inducing or inhibiting the induction of myotube contraction, wherein the analysis is carried out to determine the effect of said compounds in terms of calcium release;

identifying therapeutic compounds inducing or inhibiting the induction of myotube contraction, wherein the image analysis is carried out to determine the effect of said compounds in terms of myotube shortening and/or contraction;

identifying therapeutic compounds acting on the metabolism of skeletal muscle cells, wherein the analysis is carried out to determine the effect of said compounds in terms of glucose uptake, mitochondrial potential, and/or lactate deshydrogenase enzymatic activity.

BRIEF DESCRIPTION OF THE DRAWINGS

Further features and advantages of the invention will be apparent from the following detailed description, referring to the appended drawings wherein:

FIGS. 3A to 3E are examples of identified calcium release inducers within myotubes for the contraction cell based assay. Myotubes differentiated from healthy donors are cultured during 5 days and stained with a calcium sensitive probe, Fluo-4. Acetylcholine (20 µM), 4-chloro-m-cresol (400 µM), caffeine (10 mM), KCl (20 mM) and IGF-1 (37 nM) treatments are respectively shown. Arrows indicate when calcium release inductors are added to the myotube culture, n=3 wells;

FIGS. 4A to 4C illustrate examples of results from time course experiments identifying calcium release inhibitors after contraction induction due to acetylcholine (20 µM) treatment of myotubes from healthy donor cultured during 5 days and stained using Fluo-4 probe. Results from verapamil (40 µM), nifedipine (40 µM) and nicardipine (40 µM) treatments are shown, n=3 wells;

FIGS. 5A to 5D are examples of hit validation results from time course experiments assessing NMJ poisoning compounds through acetylcholine receptors specific inhibition. Calcium release was induced thanks to acetylcholine (20 µM) or 4-chloro-m-cresol (400 µM) within myotubes from healthy donor cultured during 5 days after a pre-treatment with inhibitors of the NMJ. Results from tubocurarine (100 µM) and succinylcholine (25 µM) treatments are shown, n=3 wells;

FIG. 6 shows the range of detection of the morphology assay. TGF-β, IGF-1, myostatin and trichostatin A treatment, in dose response, is realized on myotubes differentiated from healthy donors and cultured during 5 days. Compound effect on myotube morphology is measured according to an embodiment of the invention. "Total tube area" as well as "number of nuclei" readouts are quantified and compared to a control untreated condition set to 100%, n=3 wells;

FIGS. 7A to 7C describe the assay estimating compound effect on the rescue of muscle disuse or wasting. (A) Histogram summarizing dexamethasone (100 µM), myostatin (4.8 nM), IL1-β (1.16 nM) and TNF-α (115 pM) reference compound efficacy on myotube morphology to mimic muscle disuse or wasting. As an example of screening result, IGF-1 (18.75 nM), trichostatin A (300 nM) and follistatin (63.5 µM) effect on atrophy model is presented. (B) and (C) respectively show detailed dose responses of IGF-1 and trichostatin A rescue effect on the atrophy mediated by dexamethasone (100 µM) treatment. *, $p<0.001$, , $p<0.01$ by two way ANOVA and Tukey's multiple comparison, n=3 wells;

FIG. 8A is a quantification of some relevant morphological parameters discriminating myotubes from healthy, and DMD donors cultured in control and IGF-1 (37 nM) conditions. FIG. 8B is an example of a screening result using two DMD therapeutic compounds: prednisone (500 nM) and deflazacort (50 nM) to estimate the level of rescue compared to myotube differentiated from a healthy donor. ***, $p<0.001$, *, $p<0.05$ by two way ANOVA and Tukey's multiple comparison, n=5 wells;

DETAILED DESCRIPTION OF EMBODIMENTS OF THE INVENTION

Figure 1:
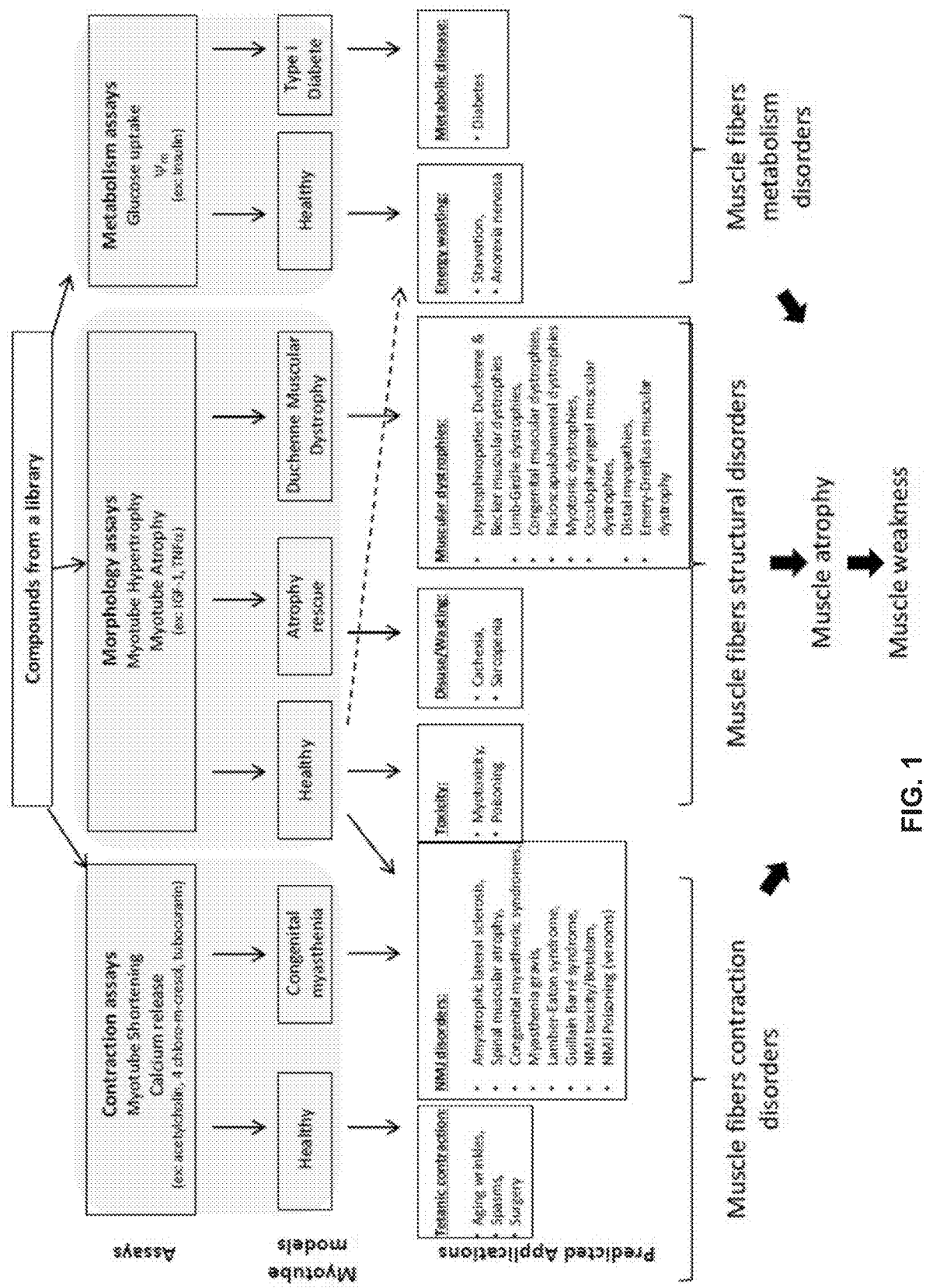
FIG. 1 illustrates the invention as a screening platform allowing the prediction of compound efficacy on disorders linked with muscle weakness though dedicated cell models and a large panel of high throughput cell based assays assessing myotube contraction, morphology, and metabolism.

The invention provides a method of drug discovery to screen a drug candidate library through a high throughput platform in order to predict a potential compound efficacy on disorders resulting in muscle weakness. As shown in FIG. 1, each compound of the library is tested though a panel of assays using dedicated cell models recapitulating distinct subclasses of muscle weakness: contraction disorders, abnormalities in fiber morphology, and metabolism dysregulation.

One advantage of the invention is that results from this screening method, not only estimates a potential efficacy of drug candidates on a muscle weakness model as usually, but allows a detailed characterization of compound mode of action on subclasses of muscle weakness.

Another advantage is that the screening method according to the invention enables an extrapolation of said compound efficacy from tested model to related disorders of said subclass.

The screening method typically comprises the following steps which are carried out in vitro.

Myogenic cells, including myoblasts can be obtained from a healthy human donor or a donor affected by a targeted muscle disorder, from a cell line, an isogenic cell line, or differentiated stem cells (including IPs, ES) recapitulating a targeted pathology. Obtaining the myoblasts is a preliminary step that is not included in the present invention.

Myogenic cells can be seeded on a device ensuring a spatial confinement of cell culture, including patterning or bioprinting technologies.

As known in the art, devices compatible with high throughput screening are microplates comprising a plurality of wells—typically, 96 or 384 wells.

Myotube morphological properties are strongly influenced by the shape of the pattern on which they are grown, this technique ensures physical constraint guidance to the cells and dedicated designs can provide a standardize the cultured myotubes through normalizing their morphological parameters.

Regarding the patterning process, advantageous embodiments of the pattern are described in connection with FIGS. 2A-2D of patent application No. PCT/EP2014/078129 in the name of the Applicant.

Bioprinting process is the use of a bioprinter to generate an in vitro culture from a bio-ink, composed of mix of cells and extracellular matrix proteins. The bioprinting process can be tailored to produce micro-scale tissues in multi-well format and resulting cultures can be confined within the extracellular deposit provided by the bio-ink.

Myogenic cells are cultured in a differentiation medium so as to promote their differentiation into myotubes.

At a given time, at least one compound or a mixture of compounds is added to the cell culture. The addition of the compound may be carried out at the beginning of myoblasts culture, during incubation of the myoblasts or once the myotubes are mature. The skilled person is able to select the appropriate time of addition of the compound depending on the assay.

After a determined incubation time of the myotubes with said compound, image processing and/or biochemical analysis of the myotubes is carried out to determine the effect of said compound on the myotubes. The incubation time depends on the experimental protocol and on the cell type. This incubation time is typically comprised between 2 and 15 days, preferably between 2 and 6 days for human myotubes.

Contraction Assays:

According to a first embodiment, the invention provides a method for screening compounds using cell based assays allowing the detection of drugs impacting muscle contraction disorders.

This method may comprise, in myotube culture step, adding at least one inhibitor of muscle contraction, or performing a genetic modification, to mimic neuromuscular disease, poisoning, or muscular genetic disease.

In particular, compounds affecting the contraction of myotubes especially from healthy donors are predicted to be candidates as new treatments for tetanic related disorders, as muscle relaxants for surgery, anti-spasmodics, and anti-wrinkles.

A high throughput cell based assay is designed to assess compounds effect on muscle contraction through estimating myotube shortening and calcium release.

By "myotube shortening" is meant myotube becoming shorter in area due to a compound treatment.

By "calcium release" is meant calcium ions entry within myotube cytoplasm due to a compound treatment.

Figure 2A:
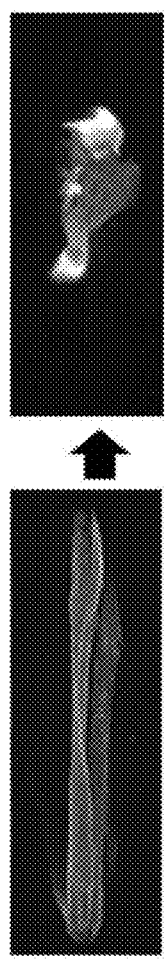
FIGS. 2A to 2C present the high throughput cell based assay dedicated to predict compounds effect on myotube contraction. (A) Myotube shortening after 4-chloro-m-cresol induction. Micrographies of troponin T immunostaining of myotubes differentiated from healthy donors cultured during 5 days by using the method according to the invention, with or without contraction induction through 4-chloro-m-cresol treatment. (B) Readouts mainly used to assess myotube shortening. (C) Representative results from myotube shortening assay. ***, $p<0.001$ by Student-t test with Holm-Sidak comparison, n=12 wells.
Figure 2B:
Figure 2C:
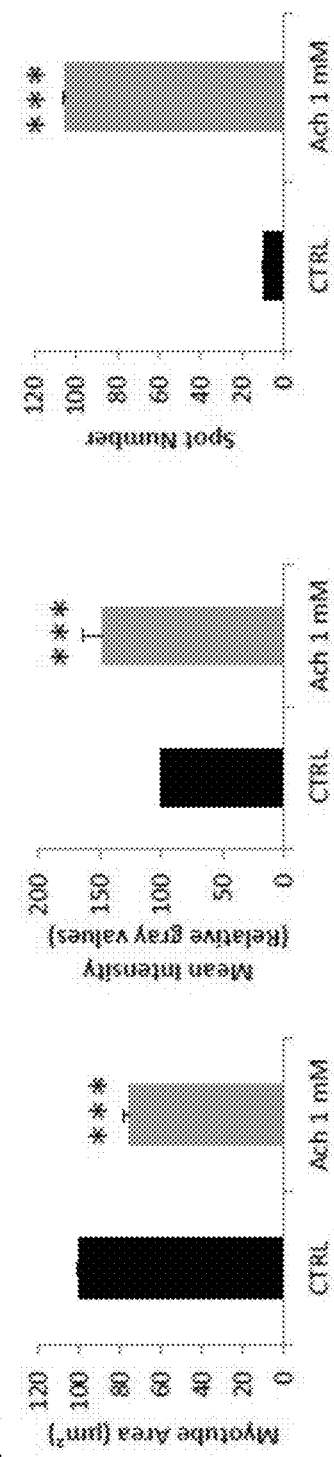

FIG. 2A shows representative myotubes after myotube shortening induction through 4-chloro-m-cresol treatment. Human primary myoblasts (HSMM, Lonza) are cultured on fibronectin coated surfaces within growth medium (Lonza SkGM™-2 cell culture Kit) during 24 hours. Then cells are cultured within differentiation medium (DMEM/F12, 2% Horse Serum, 0.5% P/S) for 5 days. Compounds (4-chloro-m-cresol, 1.5 mM) are added to myotubes during 3 minutes. Cells are fixed and an immunostaining is realized against troponin T and nuclei. Images are acquired using an Operetta high content imaging system (PerkinElmer). Automated image segmentation and analysis methods has been developed by the inventors using the Acapella software library (PerkinElmer). Then, objects are analyzed to extract basic parameters such as myotube count, nuclei count, myotube morphology (including their length, width, area), fusion index (through the percentage nuclei embedded within myotubes). However, the main descriptor of myotube shortening is the quantification of the number of spots, which are objects obtained due to myotube detachment from the culture device and subsequent folding of at least one extremity of the myotube on itself (FIG. 2B, right). Taking said parameters into account, aberrant myotubes are removed. An advanced descriptor is additionally measured, as the number of myotubes encompassing a length lower than 470 µm. FIG. 2C shows representative results of the image processing. As myotubes treatment with 4-chloro-m-cresol induces 25% decrease in tube area, and 50% increase in staining intensity readouts, the use of spot number quantification largely increases the assay window (1000%) with a reduced variability, ensuring a full compatibility of the assay with compounds screening (Z'-factors higher than 0.7).

As myotube shortening can also take origin from compound toxicity, physiological cues of myotube contraction need to be validated. Hit validation is performed using a secondary assay estimating the level of calcium release to myotube cytoplasm. Myotubes differentiated from donors are cultured during 5 days and stained with a calcium sensitive florescent probe Fluo-4 (2 µM) in a dedicated buffer (145 mM NaCl, 5 mM KCl, 1 mM $CaCl_2$, 1 mM $MgCl_2$, 5.6 mM glucose, 10 mM Hepes, pH 7.4). A single compound is added to cultured myotubes and a time-lapse acquisition is performed during 30 seconds (Eclipse-Ti, Nikon), by taking a picture each second, to follow the increase in fluorescence intensity of the probe due to calcium entry into the cytoplasm. After fluorescence background removal, a relative fluorescence intensity is calculated in the whole myotubes for each timepoint, normalizing to the first value set up at 100%. FIGS. 3A to 3E respectively show results of acetylcholine, 4-chloro-m-cresol, caffeine, KCl and IGF-1 treatments. In contrary to an hypertrophic compound (IGF-1) which only increases by 20% the relative fluorescence intensity and fails to ignite calcium release, true positive reference compounds for muscle contraction promote a single typical peak of calcium which raises from 55% (caffeine) up to 305% (acetylcholine) compared to steady state level [21, 22]. By validating myotube shortening hits with the calcium release assay, true compounds inducers of muscle contraction can be identified.

Another possible application is the identification of compounds regulating myotube contraction from donors affected by neuromuscular junction (NMJ) disorders. Compounds effect restoring neurotransmission by bypassing a structurally injured NMJ, i.e. myotubes from donors with a congenital myasthenia syndrome, a muscle specific NMJ pathology, can be predicted as new candidates to cure other related disorders, as amyotrophic lateral sclerosis, spinal muscular atrophy, myasthenia gravis, Lamber-Eaton syndrome, Guillain Barré syndrome, NMJ toxicity (Botulism), NMJ Poisoning (venoms).

Inhibitors of muscle contraction, as well as muscle relaxant molecules, are characterized by using a similar approach as the one previously described for myotube shortening and calcium release. Myoblasts are differentiated during 5 days in culture, then potential inhibitors are added in calcium buffer 15 minutes before an acethycholine treatment. FIGS. 4A to 4C illustrate examples of the calcium release inhibition due to reference compounds [23]. Verapamil, nifedipine and nicardipine treatments respectively decreases by 90%, 65% and 91%, in a dose dependent manner, the relative fluorescence intensity after acethycholine induction, demonstrating their inhibitory effect on calcium release. Moreover mode of action characterization can be optimized by comparing a compound effect on both acethycholine and 4-chloro-m-cresol inductions. FIGS. 5A to 5D show results of tubocurarine and succinylcholine effects on both acethycholine and 4-chloro-m-cresol inductions. Tubocurarine and succinylcholine reduces by 96% and 94% acethycholine induction, respectively, without clearly affecting 4-chloro-m-cresol one (0% and −30%, respectively). As acethycholine is known to provoke calcium release by interacting with a specific membrane receptor and 4-chloro-m-cresol to be an activators of the ryanodine-sensitive $Ca^{2+}$ release channel, the specific inhibition of acethycholine by tubocurarine and succinylcholine allow us to predict these two inhibitors as NMJ poisons [24]. Even if a time-lapse method is described here using a classical widefield microscope, this embodiment of the invention is fully compatible with kinetic plate readers systems allowing automated calcium flow measurements, including the Hamamatsu FDSS.

Morphology Assays:

According to a second embodiment, the invention provides a method for screening compounds using cell based assays allowing the detection of drugs impacting myotube morphology.

This method may comprise, in myotube culture step, adding at least one muscle atrophic inducer, or performing a genetic modification, to said culture to mimic muscle wasting, disuse, or muscular genetic disease.

In particular, compounds affecting myotube morphology from healthy donors are predicted to be muscle toxic compounds.

By muscle toxic is meant in the present text the effect of a compound on myoblasts differentiation, myotube maturation, myotube hypertrophy, myotube atrophy, cell viability or creatine kinase release.

By myotube maturation, it means the number of nuclei within myotubes, the rate of myotubes with aligned nuclei, the expression of maturation markers (SERCA1, RyR1, triadin, Troponin T, α-actinin, myosin heavy chain), the rate of myotubes with a respective localization of said biomarkers comparable to in vivo adult tissue (i.e. biomarker striation).

In this regard, the invention provides a method for identifying therapeutic compounds acting on atrophy or hypertrophy of skeletal muscle cells and in particular myotubes or myoblasts.

FIG. 6 shows representative measures of myotube area after increasing doses treatment of atrophic and hypertrophic reference compounds (respectively TGF-β, IGF-1, myostatin, trichostatin A) using the invention. Human primary myoblasts (HSMM, Lonza), from a healthy donor, are cultured on fibronectin coated surfaces within growth medium (Lonza SkGM™-2 cell culture Kit) during 24 hours. Then cells are cultured within differentiation medium (DMEM/F12, 2% Horse Serum, 0.5% P/S) for 24 hours. Compounds are added to the forming myotubes during 96 hours. Cells are fixed and an immunostaining is realized against troponin T and nuclei. Images are acquired using an Operetta high content imaging system (PerkinElmer).

In order to characterize compounds mode of action on the myotube model (including myoblasts differentiation, myotube maturation, myotube hypertrophy, myotube atrophy, or cell viability), automated image segmentation and analysis methods has been developed by the inventors using the Acapella software library (PerkinElmer).

First, customized segmentations of myotubes and nuclei are performed.

Second, objects are analyzed to extract basic parameters such as myotube count, nuclei count, myotube morphology (including their length, width, area, and orientation), fusion index (through the percentage nuclei within myotubes). Taking said parameters into account, aberrant myotubes are removed.

FIG. 6 is a representative result of the image processing. As illustrated by TGF-β and IGF-1 treatments respectively, atrophic and hypertrophic reference compounds are detected by down- and up-regulation of the myotube area without nuclei count alteration compared to the untreated control condition. Moreover, regarding the decrease in nuclei count after myostatin treatment at high concentration, a hallmark of cell death, an atrophy mediated by cytotoxicity can be discriminated from a true reduction of myotube area. Finally atrophy/hypertrophy biphasic effects, depending on the dose, can be detected as illustrated by trichostatin A treatment. As Z' factors are up to 0.3, this part of the invention is fully compatible with screening.

Another possible application is to mimic muscle wasting disorders (cachexia, sarcopenia) by chemically inducing atrophy on myotubes from healthy donors and then to screen compounds potentially rescuing the atrophic phenotype. As patients suffering from a large decrease in muscle mass, primary myoblast samples or myofibers can't be collected for ethical reasons and artificial in vitro strategies are necessary. Nonetheless, signaling pathways impacted in cachexia and sarcopenia are well described in the literature implicating three major cascades: glucocorticoid, Smad2/3 and the NF-κB pathway [25, 26, 27]. Molecules known to reproduce these molecular mechanisms can therefore be used to simulate pathological myotubes. For example, glucocorticoid pathway can be mimicked by dexamethasone treatment, Smad2/3 pathway by myostatin and TGF-β treatments, and NF-κB pathway by IL1-β and TNF-α treatments.

To do so, human primary myoblasts (HSMM, Lonza), from a healthy donor, are cultured on fibronectin coated surfaces within growth medium (Lonza SkGM™-2 cell culture Kit) during 24 hours. Then cells are cultured within differentiation medium (DMEM/F12, 2% Horse Serum, 0.5% P/S) for 24 hours. Candidates with potential rescue effect are added to the forming myotubes 15 minutes before the atrophic inducer. Then myotubes are cultured during 96 hours. Cells are fixed and an immunostaining is realized against troponin T and nuclei. Images are acquired using an Operetta high content imaging system (PerkinElmer). Automated image processing has been developed by the inventors using the Acapella software library (PerkinElmer).

FIG. 7A shows the atrophy mediated by reference compounds of previously described signalling pathways, as well as representative results of rescues by IGF-1, trichostatin A, and follistatin. After atrophy induction with the reference compounds, myotube area is reduced by 60% with dexamethasone, by 30% with myostatin, by 35% with IL1-β and by 55% with TNF-α. Rescue was obtained using IGF-1 and trichostatin A treatments. IGF-1 rescue by 275%, 71%, 85% and 89% the atrophy induced by dexamethasone, myostatin, IL1-13 and TNF-α, respectively while trichostatin A treatment rescue by 175%, 71%, 54% and 100% the atrophy mediated by dexamethasone, myostatin, IL1-13 and TNF-α, respectively. As examples, FIGS. 7B and 7C disclose the dose response of atrophy rescues due to IGF-1 and trichostatin A after dexamethasone mediated atrophy. As Z' factors for atrophy and atrophy rescue are up to 0.2, this embodiment of the invention is fully compatible with high content screening.

Another application is the identification of compounds regulating myotube morphology from donors affected by muscle dystrophies. Compounds effect restoring a myotube morphology comparable to healthy donors by bypassing the structural damages due to the pathology, i.e. myotubes from donors with the emblematic Duchenne muscular dystrophy (DMD), can be extrapolated to other related disorders as Becker muscular dystrophies, Limb-Girdle dystrophies, congenital muscular dystrophies, facioscapulohumeral dystrophies, myotonic dystrophies, occulopharyngeal muscular dystrophies, distal myopathies and Emery-Dreifuss muscular dystrophy.

Primary myoblasts isolated from DMD patients, cell lines, isogenic cell lines, stem cells derived myoblasts recapitulating DMD or Becker pathology (including IPs derived cells, ES cells), can be used with the present method to identify candidates that ultimately will lead to the discovery of new drugs having curative or palliative effects on the targeted pathology: for example compounds providing hypertrophy or increasing dystrophin or utrophin expression in myoblasts taken from patient suffering from DMD.

By "curative effects" is meant compounds treatment restoring or partially restoring a healthy phenotype.

By "palliative effects" is meant compounds improving patient quality of life, for example by reinforcing and stabilising muscles, reducing inflammation, decreasing surgery requirement.

Using previously described protocol, human primary myoblasts, are cultured on fibronectin coated surfaces within growth medium during 24 hours. Then cells are cultured within differentiation medium (DMEM/F12, 2% Horse Serum, 0.5% P/S) for 24 hours. Therapeutic drug candidates are added and myotubes are then cultured during 96 hours. Cells are fixed and an immunostaining is realized against troponin T and nuclei. Images are acquired using an Operetta high content imaging system (PerkinElmer). Automated image processing was been developed by the inventors using the Acapella software library (PerkinElmer).

FIG. 8A shows representative results of the image processing comparing myotube formation from heathy and DMD donor, with or without IGF-1 treatment, in terms of tube number, fusion index, and tube width. Tube number is decreased by 50%, fusion index by 88% and myotube width by 52% in DMD myotubes compared to healthy ones. IGF-1, a compound used in DMD treatment is shown to respectively rescue by 109%, 204% and 15% these readouts. In order to estimate the compatibility of the invention with cell based assay compound screening, Z'-factors were calculated for each readout. IGF-1 effect on DMD myotube shows a Z'-factor of 0.2 for the tube number readout, compared to an untreated condition. This validates the invention as compatible with HCS drug discovery to detect compounds efficient to treat DMD pathology. FIG. 8B shows additional examples of drugs in clinical development (prednisone and deflazacort) which consolidate the ability to detect potential therapeutic compounds from a screening using the invention. Prednisone and deflazacort present a 20% and 54% increase of tube number, respectively. Similarly, the fusion index was also increased by 28% and 59%, respectively. A 20% threshold is set by the inventors to validate a rescue by a compound. Therefore, prednisone and deflazacort would be categorized as potential candidates to treat DMD, and predict potential effect of these compounds for other dystrophies, according to the invention.

Metabolism Assays:

According to a third embodiment, the invention provides a method for screening compounds using cell based assays allowing the detection of drugs impacting muscle metabolic disorders.

This method may comprise, in myotube culture step, adding at least one inhibitor of muscle metabolism, or performing a genetic modification, to said culture to mimic metabolism disease, or muscular genetic disease.

In particular, compounds enhancing myotube metabolism from healthy donors or type I diabetic donors are predicted to be cures for diabetes and to counteract the energy wasting syndrome due to for example anorexia nervosa or a deep starvation.

Human primary myoblasts from a healthy or a type I diabetic donor, are cultured on fibronectin coated surfaces within growth medium during 24 hours. Then cells are cultured within differentiation medium (DMEM/F12, 2% Horse Serum, 0.5% P/S) for 24 hours. Therapeutic drug candidates are added and myotubes are then cultured during 96 hours. Compound effect on glucose metabolism is performed by using the indications provided by the manufacturer (Glucose Uptake Colorimetric Assay Kit, Sigma).

Figure 9:
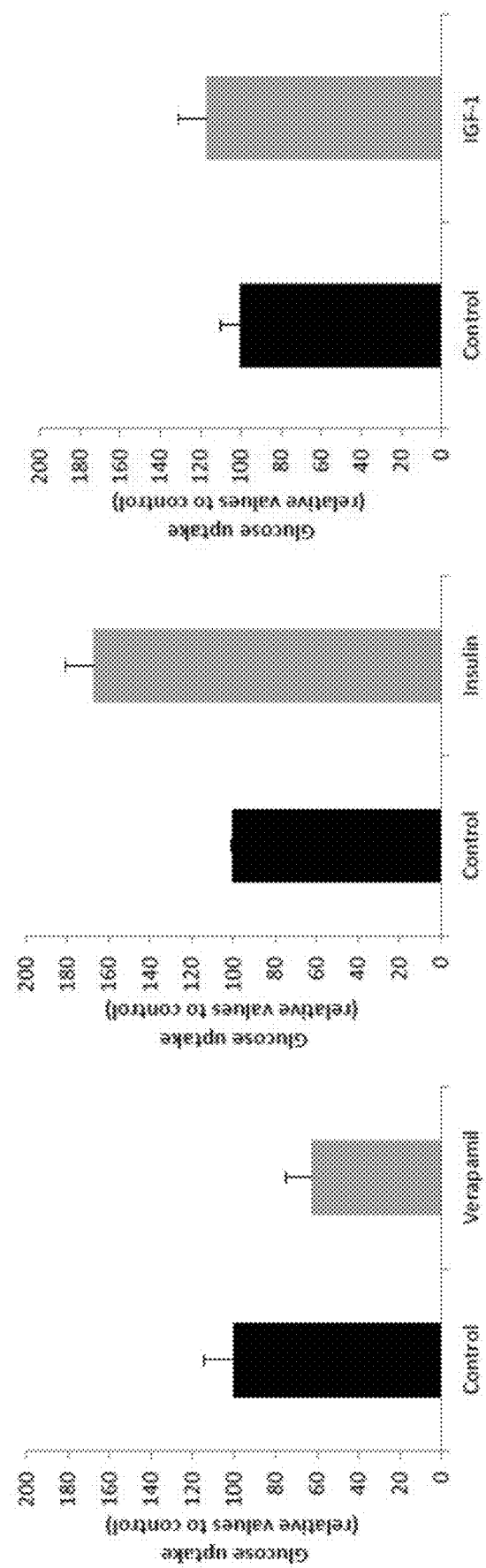
FIG. 9 is an example quantifications from the metabolic assay according to an embodiment of the invention: Glucose metabolism in myotubes differentiated from myoblasts of healthy donors according to the invention. Results of treatments with insulin (10 µM) and verapamil (125 µM) reference compounds are shown, as well as IGF-1 (37 nM) a specific treatment, n=3 wells.

FIG. 9 shows results from reference compounds effect on glucose metabolism according to the invention. Insulin increases by 67% and verapamil decreases by 37% glucose metabolism. IGF-1 has no effect on glucose uptake and validates the specificity of compound detection only affecting muscle metabolism.

Figure 10:
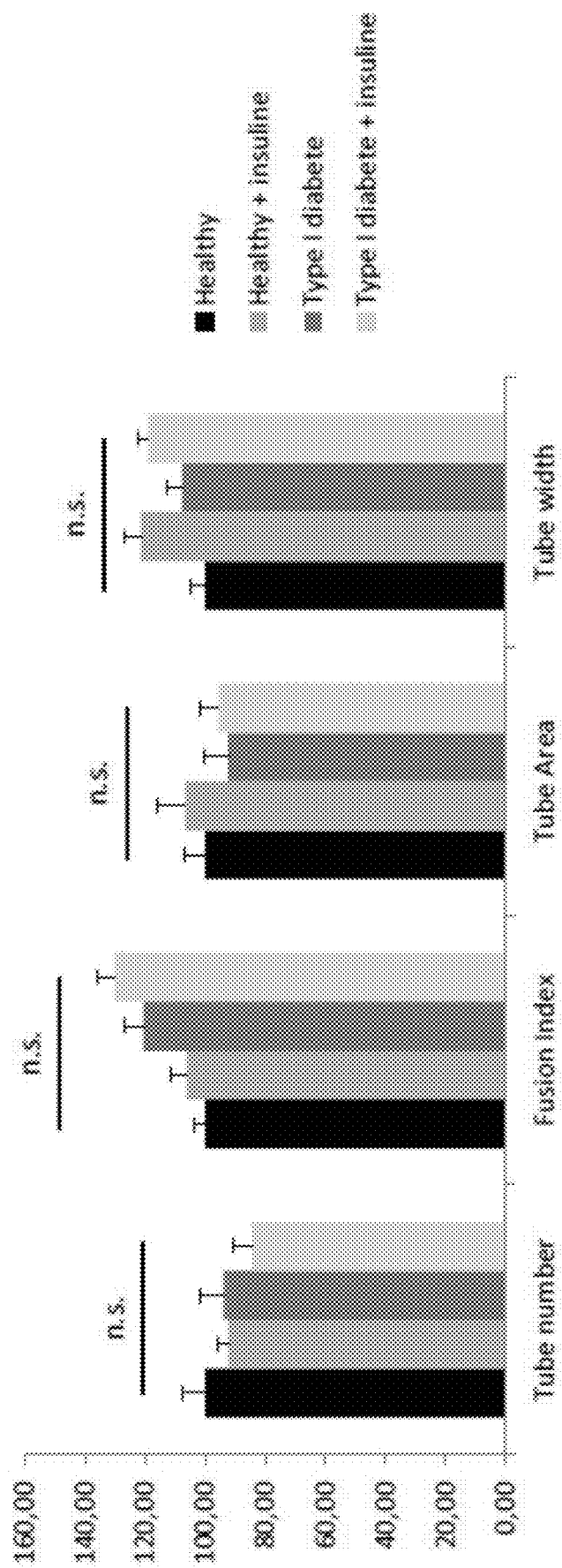
FIG. 10 is a quantification of some relevant morphological parameters, as tube number, fusion index, tube area and tube width, of myotubes from healthy and type I diabetes donors, cultured in control and insulin (10 µM) conditions according to the invention, n=10 wells.

FIG. 10 is a quantification of some relevant morphological parameters, as tube number, fusion index, tube area tube width, of myotubes from healthy and type I diabetes donors, cultured in control and insulin (10 µM) conditions according to the invention. These histograms show that myotubes differentiated from a type I diabetic donor, which are metabolically affected by the pathology, have a similar morphology compared to myotubes from healthy donors. Moreover insulin, which enhances glucose metabolism, does not modify myotube morphology. This illustrates the specificity of metabolisms assays on compounds detection and the complementarity of the approaches to detect new drugs rescuing specifically metabolic disorders.

Regarding the efficacy of IGF-1 to induce myotubes hypertrophy from healthy and DMD donors and to rescue an induced muscle wasting without providing cytotoxicity, as well as its inability to ignite myotube contraction and to directly regulate metabolism, these results show that, by using the invention, IGF-1 is predicted to be efficiently used as a cure only to treat muscle wasting disorders (cachexia, sarcopenia) as well as dystrophies.

REFERENCES

[1] May 2006 report to Congress on Implementation of the MD CARE Act, as submitted by Department of Health and Human Service's, National Institutes of Health.

[2] Lawler J M, (2011). Exacerbation of pathology by oxidative stress in respiratory and locomotor muscles with Duchenne muscular dystrophy. J Physiol. 589(Pt 9):2161-2170.

[3] Harisseh R, Chatelier A, Magaud C, Déliot N, Constantin B, (2013). Involvement of TRPV2 and SOCE in calcium influx disorder in DMD primary human myotubes with a specific contribution of α1-syntrophin and PLC/PKC in SOCE regulation. Am J Physiol Cell Physiol. 304(9): C881-894.

[4] Sharma U, Atri S, Sharma M C, Sarkar C, Jagannathan N R, (2003). Skeletal muscle metabolism in Duchenne muscular dystrophy (DMD): an in-vitro proton NMR spectroscopy study. Magn Reson Imaging. 21(2):145-153.

[5] Ha J C, Richman D P, (2015). Myasthenia gravis and related disorders: Pathology and molecular pathogenesis. Biochim Biophys Acta. 1852(4):651-657.

[6] Franssen F M, Wouters E F, Schols A M, (2002). The contribution of starvation, deconditioning and ageing to the observed alterations in peripheral skeletal muscle in chronic organ diseases. Clin Nutr. 21:1-14.

[7] Argilés J M, Busquets S, Stemmler B, López-Soriano F J, (2014). Cancer cachexia: understanding the molecular basis. Nat Rev Cancer. 14(11):754-762.

[8] Morley J E, Thomas D R, Wilson M M, (2006). Cachexia: pathophysiology and clinical relevance. Am J Clin Nutr. 83(4):735-743.

[9] Tomaszewski M, Sępień K M, Tomaszewska J, Czuczwar S J, (2011). Statin-induced myopathies. Pharmacol Rep. 63(4):859-866.

[10] Ciciliot S, Rossi A C, Dyar K A, Blaauw B, Schiaffino S, (2013). Muscle type and fiber type specificity in muscle wasting. Int J Biochem Cell Biol. 45(10):2191-2199.

[11] Valdez G, Tapia J C, Lichtman J W, Fox M A, Sanes J R, (2012). Shared resistance to aging and ALS in neuromuscular junctions of specific muscles. PLoS One. 7(4): e34640.

[12] Matsumoto T, Ikuta N, Mori M, Nagayama K, (2010). Mechanics of wrinkle formation: micromechanical analysis of skin deformation during wrinkle formation in ultraviolet-irradiated mice. Skin Res Technol. 16(2):179-89.

[13] Edens B M, Ajroud-Driss S, Ma L, Ma Y C, (2015). Molecular mechanisms and animal models of spinal muscular atrophy. Biochim Biophys Acta. 1852(4):685-692.

[14] McClorey G, Fall A M, Moulton H M, Iversen P L, Rasko J E, Ryan M, Fletcher S, Wilton S D, (2006). Induced dystrophin exon skipping in human muscle explants. Neuromuscul Disord. 16:583-590.

[15] Webster C, Blau H M, (1990). Accelerated age-related decline in replicative life-span of Duchenne muscular dystrophy myoblasts: implications for cell and gene therapy. Somat Cell Mol Genet. 16:557-565.

[16] Trendelenburg A U, Meyer A, Jacobi C, Feige J N, Glass D J, (2012). TAK-1/p38/nNFκB signaling inhibits myoblast differentiation by increasing levels of Activin A. Skelet Muscle. 2:3.

[17] Trendelenburg A U, Meyer A, Rohner D, Boyle J, Hatakeyama S, Glass D J, (2009). Myostatin reduces Akt/TORC1/p70S6K signaling, inhibiting myoblast differentiation and myotube size. Am J Physiol Cell Physiol. 296: 01258-1270.

[18] Vandenburgh H, Shansky J, Benesch-Lee F, Barbata V, Reid J, Thorrez L, Valentini R, Crawford G, (2008). Drug-screening platform based on the contractility of tissue-engineered muscle. Muscle Nerve. 37:438-447.

[19] Vandenburgh H, Shansky J, Benesch-Lee F, Skelly K, Spinazzola J M, Saponjian Y, Tseng B S, (2009). Automated drug screening with contractile muscle tissue engineered from dystrophic myoblasts. FASEB J. 23:3325-3334.

[20] Purslow P P, (2010). Muscle fascia and force transmission. J Bodyw Mov Ther. 14:411-417.

[21] Ducreux S, Zorzato F, Müller C, Sewry C, Muntoni F, Quinlivan R, Restagno G, Girard T, Treves S, (2004). Effect of ryanodine receptor mutations on interleukin-6 release and intracellular calcium homeostasis in human myotubes from malignant hyperthermia-susceptible individuals and patients affected by central core disease. J Biol Chem. 15:43838-43846.

[22] Heunks L M, Machiels H A, Dekhuijzen P N, Prakash Y S, Sieck G C, (2001). Nitric oxide affects sarcoplasmic calcium release in skeletal myotubes. J Appl Physiol. 91:2117-2124.

[23] Nott M W. Drugs on skeletal muscle. Pharmacology. Vol II.

[24] Clausen T, Gissel H, (2005). Role of Na,K pumps in restoring contractility following loss of cell membrane integrity in rat skeletal muscle. Acta Physiol Scand. 183: 263-271.

[25] Argilés J M, Busquets S, Stemmler B, López-Soriano F J, (2014). Cancer cachexia: understanding the molecular basis. Nat Rev Cancer. 14(11):754-762.

[26] Iezzi S, Di Padova M, Serra C, Caretti G, Simone C, Maklan E, Minetti G, Zhao P, Hoffman E P, Puri P L, Sartorelli V, (2004). Deacetylase inhibitors increase muscle cell size by promoting myoblast recruitment and fusion through induction of follistatin. Dev Cell. 6:673-684.

[27] Sakuma K, Yamaguchi A, (2012). Novel intriguing strategies attenuating to sarcopenia. J Aging Res. 2012: 251217.

The invention claimed is:

1. A method for high throuphput screening compounds, comprising:
   (i) providing an in vitro culture of myotubes, wherein the in vitro myotubes culture is obtained by the following method:
      providing a cell culture device allowing the culture of myoblasts or myotubes,
      depositing said cells (a) from a human donor or human group of donors in good health, (b) from a human donor or human group of donors affected by a muscle related disorder, or (c) from primary cells, a cell line, an isogenic cell line or differentiated stem cells recapitulating a muscle disorder, on said culture device by using a method allowing a spatial control of cell culture, and
      culturing said cells during a determined incubation time so as to promote a spatially controlled myotube culture,
   (ii) adding at least one compound to said culture,
   (iii) after a determined incubation time of the myotubes with said compound, carrying out structural and functional readouts of the myotubes to determine an effect of said compound on the myotubes, said functional readouts comprising calcium release, and resulting myotube shortening in a high throughput assay through quantification of the number of immunostained troponin-T spots corresponding to detachment and folding of at least one extremity of the myotubes, and
   (iv) based on said determined effect, predicting ability of said compound to improve or alter healthy muscle features, or to treat, rescue, or cure muscle disorders, said features or said disorders being linked with muscle contraction, muscle morphology or muscle metabolism.

2. The method according to claim 1, further comprising, in myotube culture step, adding at least one muscle atrophic inducer, or performing a genetic modification, to said culture to mimic muscle wasting, disuse, or muscular genetic disease.

3. The method according to claim 1, further comprising, in myotube culture step, adding at least one inhibitor of muscle contraction, or performing a genetic modification, to said culture to mimic neuromuscular disease, poisoning, or muscular genetic disease.

4. The method according to claim 1, further comprising, in myotube culture step, adding at least one inhibitor of muscle metabolism, or performing a genetic modification, to said culture to mimic metabolic disease or a muscular genetic disease.

5. The method according to claim 1, wherein the method allowing the spatial control of cell culture includes bioprinting.

6. The method according to claim 1, wherein the cell culture device comprises a substrate and at least one cell-adhesive pattern, myoblasts from a human donor or group of human donors, in good health or affected by a emblematic muscle disorder, from a cell line, an isogenic cell line or differentiated stem cells recapitulating a muscle disorder are deposited on the at least one cell-adhesive pattern, and said myoblasts are cultured in a differentiation medium during a determined incubation time so as to promote cell differentiation into myotubes.

7. The method according to claim 6, wherein the substrate is selected from:
a hard substrate; and
a soft substrate wherein the Young's modulus of the substrate is comprised between 5 and 15 kPa.

8. The method according to claim 1, comprising carrying out image analysis of the myotubes to measure morphological changes in skeletal muscle cells, myotubes or myoblasts, said measured morphological changes comprise area and maximal width of the myotubes after incubation with the compound and wherein image analysis comprises myotube image binarization, computation of a distance map of said myotubes and computation of the maximal width of each myotube from said distance map.

9. The method according to claim 1, wherein said functional readouts comprise biomarkers of myotube maturation, through the expression and localisation of myosin heavy chain, troponin T, dystrophin, alpha-syntrophin, dystroglycans, acethycholin receptors, Smad 2/3, and/or NF-κB.

10. The method according to claim 1, wherein said functional readouts comprise myotube metabolism through the quantification of glucose uptake, mitochondrial potential, and/or lactate deshydrogenase in a high throughput assay.

11. The method according to claim 8, in the field of drug discovery, for identifying therapeutic compounds acting on atrophy or hypertrophy of skeletal muscle cells, wherein the image analysis is carried out to determine the effect of said compounds in terms of atrophic or hypertrophic properties.

12. The method according to claim 9, in the field of drug discovery, for identifying therapeutic compounds acting on the maturation of skeletal muscle cells, wherein an automated analysis is carried out to determine the effect of said compounds in terms of said specific biomarkers expression and/or localisation.

13. The method according to claim 1, for identifying therapeutic compounds inducing or inhibiting the induction of myotube contraction, wherein an analysis is carried out to determine effect of said compounds in terms of calcium release.

14. The method according to claim 1, in the field of drug discovery, for identifying therapeutic compounds inducing or inhibiting the induction of myotube contraction, wherein the image analysis is carried out to determine the effect of said compounds in terms of myotube shortening and/or contraction.

15. The method according to claim 10, in the field of drug discovery, for identifying therapeutic compounds acting on the metabolism of skeletal muscle cells, wherein the analysis is carried out to determine the effect of said compounds in terms of glucose uptake, mitochondrial potential, and/or lactate deshydrogenase enzymatic activity.

16. The method according to claim 1, wherein the cell culture device is a microplate.

* * * * *

UNITED STATES PATENT AND TRADEMARK OFFICE
CERTIFICATE OF CORRECTION

PATENT NO. : 11,061,017 B2
APPLICATION NO. : 15/736841
DATED : July 13, 2021
INVENTOR(S) : Sébastien Degot et al.

Page 1 of 1

It is certified that error appears in the above-identified patent and that said Letters Patent is hereby corrected as shown below:

In the Specification

Column 4,
Line 49, "NF-κ3" should read --NF-κB--.

Column 11,
Line 2, "IL1-13" should read --IL1-β--.
Line 4, "IL1-13" should read --IL1-β--.

Column 13,
Line 25, "Sępień K M," should read --Stępień K M,--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*